(12) United States Patent
Matsuoka (10) Patent No.: US 6,501,544 B2
(45) Date of Patent: Dec. 31, 2002

(54) INSPECTION APPARATUS FOR SURFACES OF SPHERES

(75) Inventor: Mitsuhiro Matsuoka, Daito (JP)

(73) Assignee: Amatsuji Steel Ball Mfg. Co., Ltd., Osaka (JP)

( * ) Notice: Subject to any disclaimer, the term of this patent is extended or adjusted under 35 U.S.C. 154(b) by 0 days.

(21) Appl. No.: 09/906,536

(22) Filed: Jul. 16, 2001

(65) Prior Publication Data

US 2002/0135756 A1 Sep. 26, 2002

(51) Int. Cl.[7] .......................... G01N 21/00; B07C 5/00
(52) U.S. Cl. ................... 356/237.1; 356/237.2; 209/565; 209/524
(58) Field of Search ..................... 356/237.1, 237.2, 356/239.1, 239.2, 239.3, 239.8, 240.1, 237.5; 209/524, 538, 580, 565, 587, 631

(56) References Cited

U.S. PATENT DOCUMENTS 3,565,248 A * 2/1971 Messerschmidt ............ 209/524
3,581,888 A * 6/1971 Kelly et al. ................. 209/565
6,346,982 B1 * 2/2002 Yasuda et al. ............ 356/237.1

* cited by examiner

*Primary Examiner*—Georgia Epps
*Assistant Examiner*—Tim Thompson
(74) *Attorney, Agent, or Firm*—Flynn, Thiel, Boutell & Tanis, P.C.

(57) ABSTRACT

An apparatus for inspecting surfaces of spheres such steel balls, on which sequentiality of cleaning and screening steps is attained without danger of rusting, and inspection accuracy and efficiency are enhanced, comprises a cleaning device for cleaning the spheres on a rotary disc with rotating brushes, a mechanism for inspecting and screening the cleaned spheres in oil in terms of non-defective and defective, and a removal device for removing both spheres separately. The mechanism includes a driving roller revolving and carrying thereon each sphere, a set of control rollers making tangential contact with the sphere thrusted along the outer circumference of the driving roller, a sensor for inspecting the surface of sphere while imparting a twist toward the sensor to the sphere by rotations of the driving roller and control rollers, and an oil tank holding therein the elements above.

7 Claims, 11 Drawing Sheets

INSPECTION APPARATUS FOR SURFACES OF SPHERES

BACKGROUND OF THE INVENTION

1. Field of the Invention

This invention relates to an inspection apparatus for inspecting surfaces of spheres or spherical bodies such as steel balls to detect flaws thereby screening out.

2. Description of Related Art

With conventional inspection apparatus for surfaces of spheres, for example, steel balls for use in ball bearings, it has been a common practice to inspect the spheres in air. This inspection method is advantageous in that it is easy to handle the spheres, but the surfaces of spheres must beforehand be degreased cleanly and dried. The greasy contents, if not completely degreased, remained as stain, as a result of which not only were the stained spheres culled as rejects, but also the greasy contents were accumulated at the passageway of the inspection station, and further attached to another spheres, thus being responsible for rejects.

A complete degreasing method has been therefore investigated and for example, an attempt has been made to conduct ultrasonic cleaning with an organic solvent. According to the cleaning method in the solvent, however, aside from the fact that the substance itself may be toxic or not friendly to the earth environment, an extra device for recovery of the solvent to reduce the running cost is necessitated, thus making the overall apparatus larger. Currently, the situation is improved to some degree since several less toxic and environmentally-friendly substances have been developed, and yet the circumstances still do not change seeing that the apparatus as a whole is large-sized.

In particular, the spheres made of a metal susceptible to rusting are required to be treated as quickly as possible after degreasing lest those allowed to stand for a long time in the degreased state should not be rusted. Otherwise installation of an extra air conditioning facility is neccesitated.

In order to cope with the present situation and to overcome the problems above, the invention is designed to provide an inspection apparatus or surfaces of spheres by adopting a new approach of inspecting in an oil without causing the foregoing problems with greasy staining. Accordingly, important objects of this invention are to eliminate the necessity of degreasing, to get rid of any danger of rusting even with a metal liable to rusting, to dispense with any air-conditioning even during a long-time treatment, to enable compactization, making the installation space smaller, and to make the steps of cleaning and screening continuous thereby enhancing the workability. Another object is to heighten the efficiency and accuracy of inspection of the apparatus.

SUMMARY OF THE INVENTION

The present invention for accomplishing the aforesaid objects resides in the construction of an inspection apparatus for surfaces of spheres which comprises a combination of: a supply device for supplying the spheres to be inspected; a cleaning device for the spheres so supplied; an inspection and screening mechanism for the spheres thus cleaned and delivered through a tubing; and a removal device for removing the spheres thus inspected separately according to the screening class and housing them in separate containers. And the apparatus is characterized in that the inspection and screening mechanism includes a driving roller; alignment fingers, provided upstream of the driving roller, for putting the spheres supplied in a line one by one onto the driving roller under rotation; a feeding roller for thrusting each sphere carried on the driving roller toward the rotational direction of the driving roller; a set of conical control rollers disposed to tangentially contact with the surface of the sphere thus thrusted with an outer periphery of the driving roller, a support roller, disposed adjacent to and downstream of the control rollers, for supporting the sphere; a sensor for insecting the surface of the sphere supported on the driving roller, the set of controllers, and the support roller; a discriminating gate disposed at the output side of the support roller; and an oil tank holding therein the driving roller, the feeding roller, the set of control rollers, the support roller, the sensor and the discriminating gate so that the surfaces of the spheres can be inspected in the oil thereby to discriminate and screen the spheres in terms of non-defective and defective.

According to another embodiment, the apparatus is further characterized in that the cleaning device includes a rotary disc and a fixed disc which are superposed on each other at the surface side and reverse side, respectively of the device and held in a slanting manner, the rotary disc being defined concentrically with holes for placing therein every one of the spheres in the same pitch radially and circumferentially, the fixed disc being defined partly with a cutout for delivery of the spheres therefrom; cleaning brushes provided on and in contact with the rotary disc at a predetermined position in the rotational direction thereof so that the spheres supplied in the holes can be cleaned with the cleaning brushes with the rotation of the rotary disc and the cleaned spheres can be delivered in sequence from the cutout downwardly.

According to the apparatus of this invention stated above, the spheres loaded on the supply device are supplied to the cleaning device in a definite number and then cleaned one by one in mutually discrete state by the rotation of the cleaning brushes. The cleaned spheres are transferred in a line to the screening mechanism. The inspection station of the screening mechanism is located in oil where the spheres are inspected at their surfaces one by one by means of the sensor and automatically screened between good or non-defective spheres and rejects or defective spheres.

The spheres thus screened are lifted up out of the oil, and those non-defective are coated with a rust-proof oil and then recovered into a container of the removal device while the rejects are recovered to another container.

More specifically stated, in the cleaning device constructed above, the spheres supplied quantitatively roll by their own weights thereby to enter into the holes of the rotary disc under revolution. Here, being apertured concentrically in the same pitch radially and circumferentially the spheres are guided through a chute, which is provided with guide grooves so as to adapt to the radial pitch of the spheres, into the holes. The spheres entering into the holes of the rotary disc under revolution are conveyed sequentially to the position of the brushes and cleaned, while being rotated neary one turn, with the brushes under rotation.

The cleaned spheres are withdrawn out of the cutout of the fixed disc downwardly, aligned in a line with the aid of the alignment device, and delivered in a line toward the next inspection station.

At the inspection and screening mechanism, the spheres thus traded in a line from the cleaning device are supplied, at the top of a chute, through alignment fingers for aligning the flow of spheres and feed rollers one by one to an inspection spot.

Here, the operation is conducted in the following manner: When the alignment fingers ascend, one sphere passes. And the alignment fingers revert to the original position, thus stopping another sphere next to the sphere from flowing. The sphere being carried on the driving roller is forced into the inspection spot with the aid of the feed roller revolving concentrically with the driving roller. At the inspection spot, the sphere is supported by four points of the driving roller, the set of control rollers and the support roller.

The driving roller revolves in the progress direction, whose rotation force is transmitted to the sphere and further rotates the set of control rollers making in tangential contact with the sphere. The control rollers assume a conical form and are provided, at their tops opposite to their conical sides, with gears so that their movement may be transmitted to the sphere to be inspected. The control rollers are needed to revolve lightly and silently, and to that end, the gears are of eccentric helical gears having an eccentricity of the same magnitude. The eccentricity imparts a twist to the sphere and the sphere imparted with the twist moves to the sensor, which serves, in turn, to inspect the front surface of the sphere.

After inspection, the sphere is discriminated in terms of non-defective or defective on an electric circuit, which moves the support roller so as to discharge the sphere from the inspection spot and screens out with the discriminating gate.

BRIEF DESCRIPTION OF THE DRAWINGS

The invention will be hereinafter described in more detail with reference to the accompanying drawings, in which.

DESCRIPTION OF THE PREFERRED EMBODIMENTS

Figure 1:
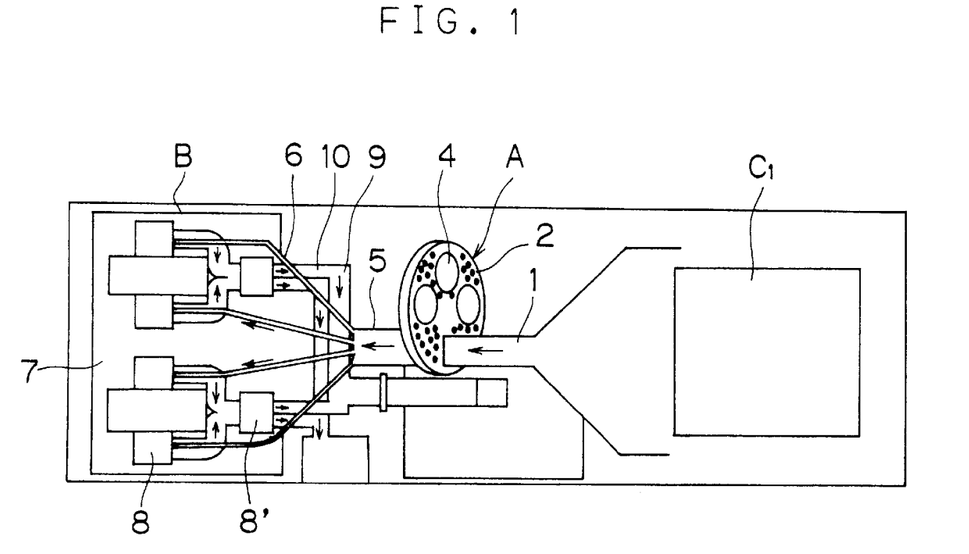
FIG. 1 is a schematic plan view showing an overall inspection apparatus for inspecting surfaces of spheres pertaining to this invention.
Figure 2:
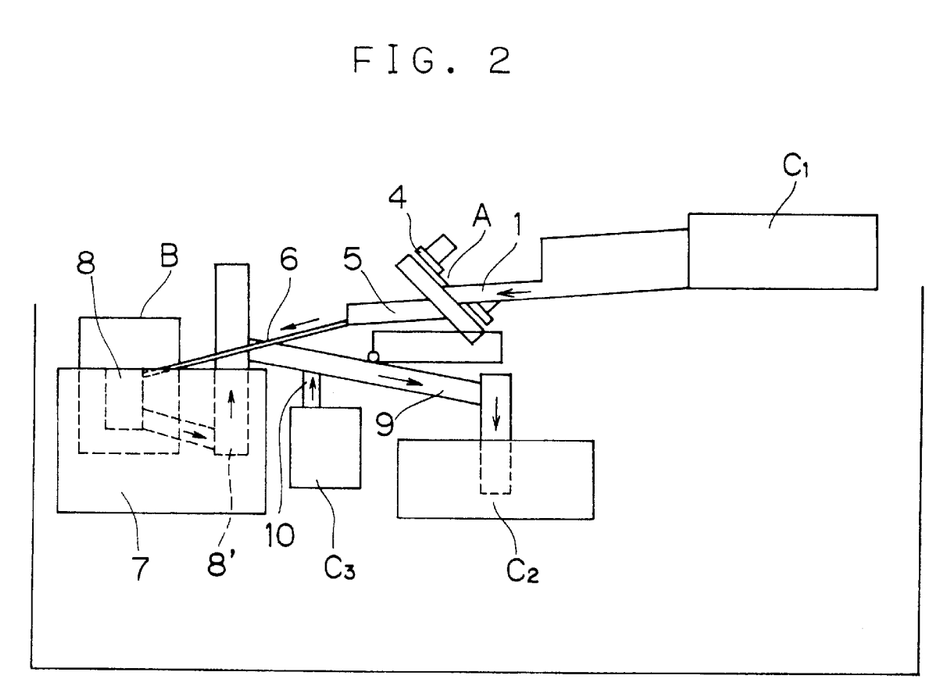
FIG. 2 is a schematic elevational view of the apparatus in FIG. 1.

Referring to FIGS. 1 and 2, the invention apparatus is basically constructed of a combination of: a supply device 1, a cleaning device A, an inspection and screening mechanism B, and a removal device including a lifting device 8 out of oil, a removal path 9 for non-defective spheres and a removal path 10 for rejects.

The supply device 1 is usually a chute with guide grooves provided in conformity with the radial pitch of sphere (cf. FIG. 3), wherein the spheres S to be inspected, housed in a container $C_1$, are quantitatively fed from the container toward the cleaning device A.

Figure 3:
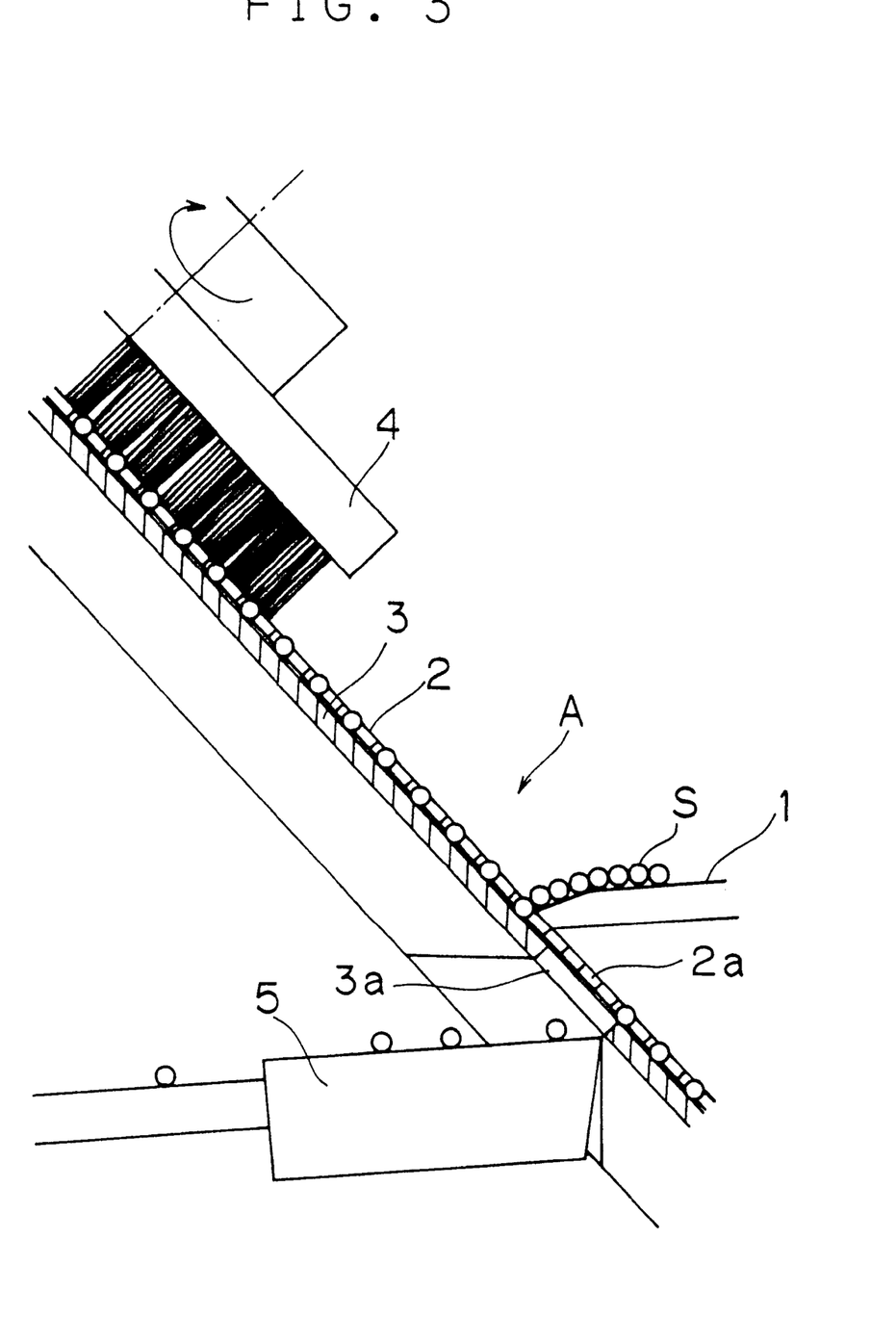
FIG. 3 is a partial diagrammatic view showing the essential parts of a cleaning device in the invention.

The cleaning device A is, as shown in FIG. 3, constructed so that a rotary disc 2 apertured with holes 2a, in each of which one sphere S is received, is superposed on a fixed disc 3 for supporting spheres S and partly pierced with a cutout 3a for removal of spheres therethrough and both discs are held at an inclination angle of ca. 45°; and that a plurality of disc-form cleaning brushes 4 (three in the figure) such as nylon brushes are disposed on the rotaty disc 2 so as to make contact with the surfaces of the spheres. The disc-form brushes 4 serve to spray a cleaning oil from their brush bristles. It is effective that the holes 2a of the rotary disc 2 be dimensioned in a diameter larger suited to hold therein each of spheres rolling down of their dead weight. They are provided concentrically in the same pitch radially and cicumferentially.

Here, in order to maximize the throughput per hour of the cleaning device, there should be no vacant hole of the disc 2 where spheres are not occupied. To that end, more spheres than the hole number of the disc 2 must be supplied to the disc 2. In that case, extra spheres cannot occupy the holes 2a and some of them may roll toward the brushes and then be bounced thereby if the disc 2 is disposed horizontally. For this reason, the disc 2 is inclined (at an angle of around 45°), whereby spheres supplied but not occupied in the holes stand by at the supply position until next unoccupied holes come and a smooth supply of spheres is made possible.

Thus the spheres are supplied, through the chute with guide grooves formed to adapt to the radial pitch of the spheres, to the holes 2a of the rotary disc 2, and some of them that cannot occupy the holes 2a of the disc 2 stagnate at the flat parts between the holes. If all the holes are located concentrically at the same pitch, those stagnating on the flat parts continue to remain there throughout without occupying the holes. If the holes are located to be deviated by half a radial pitch, those spheres on the flat parts are to be cleaned without stagnating. It is therefore preferred to provide these holes circumferentially at several places.

The thickness of the rotary disc 2 is preferred to be thin considering the cleaning ability, but usually preferred to be ½ to ⅓ the diameter of a sphere so that spheres may not come bouncingly out of the holes 2a during cleaning. The rotary disc 2 and the fixed disc 3 are usually made of oil-resistant rubber in order to avoid the occurrence of flaws.

The rotary disc 2 serves to transfer the spheres while revolving, and during nearly one revolution they are cleaned with revolving disc-like brushes 4.

The revolution number of the rotary disc 2 has relations to cleaning ability and treatment speed. The bigger the sphere, the lower is the revolution number, whereas the smaller, the higher.

The brush height of the disc-like brush 4 is such that the brush makes a slight contact with the disc 2 or spheres. After cleaning, the spheres are withdrawn out of the cutout 3a of the fixed disc 3 at the rear side downwardly, brought into line with alignment fingers 11, which will be hereinbelow described, and delivered through a withdrawal chute 5 toward four (in FIG. 1) inspection stations 8 via respective paths 6 in a line.

Figure 4:
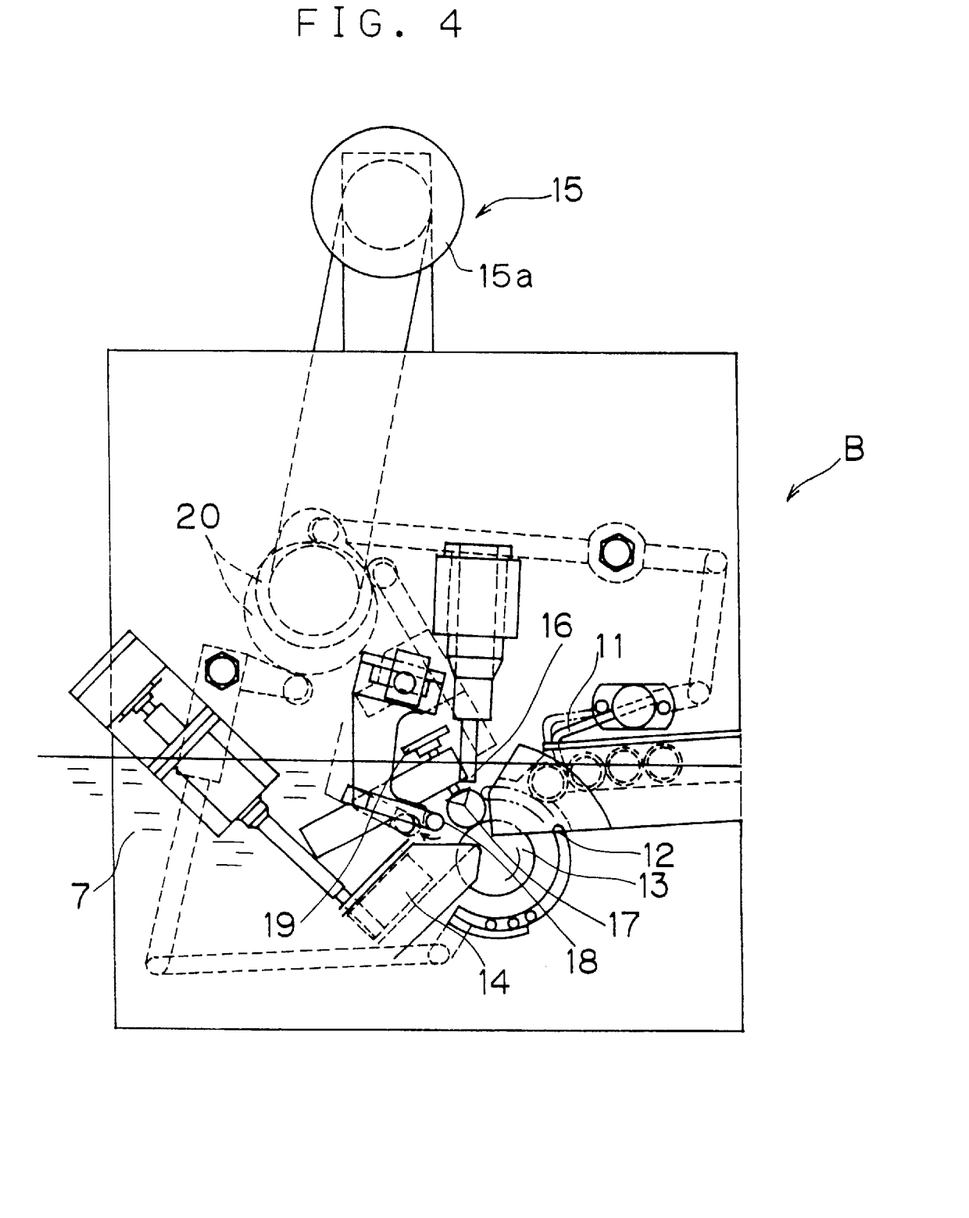
FIG. 4 is a schematic view showing the constitution of an inspection-screening mechanism according to his invention.

The inspection and screening mechanism B bears a series of steps of receiving the spheres thus delivered, inspecting and screening them between non-defective and defective ones. As depicted in FIG. 4, the mechanism B is constructed of the alignment fingers 11, a feeding roller 12, a driving roller 13, a discriminating gate 14, a sensor 16, a set of (two) control rollers 17, a support roller 18 for supporting the spheres, and a timing detector 15.

The inspection and screening mechanism B is further characterized in that of the elements mentioned above, at least, the feeding roller 12, the driving roller 13, the discriminating gate 14, the sensor 16, the set of control rollers 17 and the support roller 18 are held and arranged within an oil tank 17 below the oil level so that inspection and screening can be performed in oil.

The alignment fingers 11 are located at the upper ends of the paths 6 contiguous to the chute 5 and serve to allow the spheres S to pass therethrough one by one to put each sphere onto the driving roller 13 and after passing, to revert to the initial position thereby to avoid the intrusion of the next sphere following.

The feeding roller 12 is provided to encompass the driving roller 13 therein so as to rotate concentrically with the driving roller 13, thus forcing the sphere along the outer circumference of the driving roller 13 to the inspection spot as it rotates.

Figure 5:
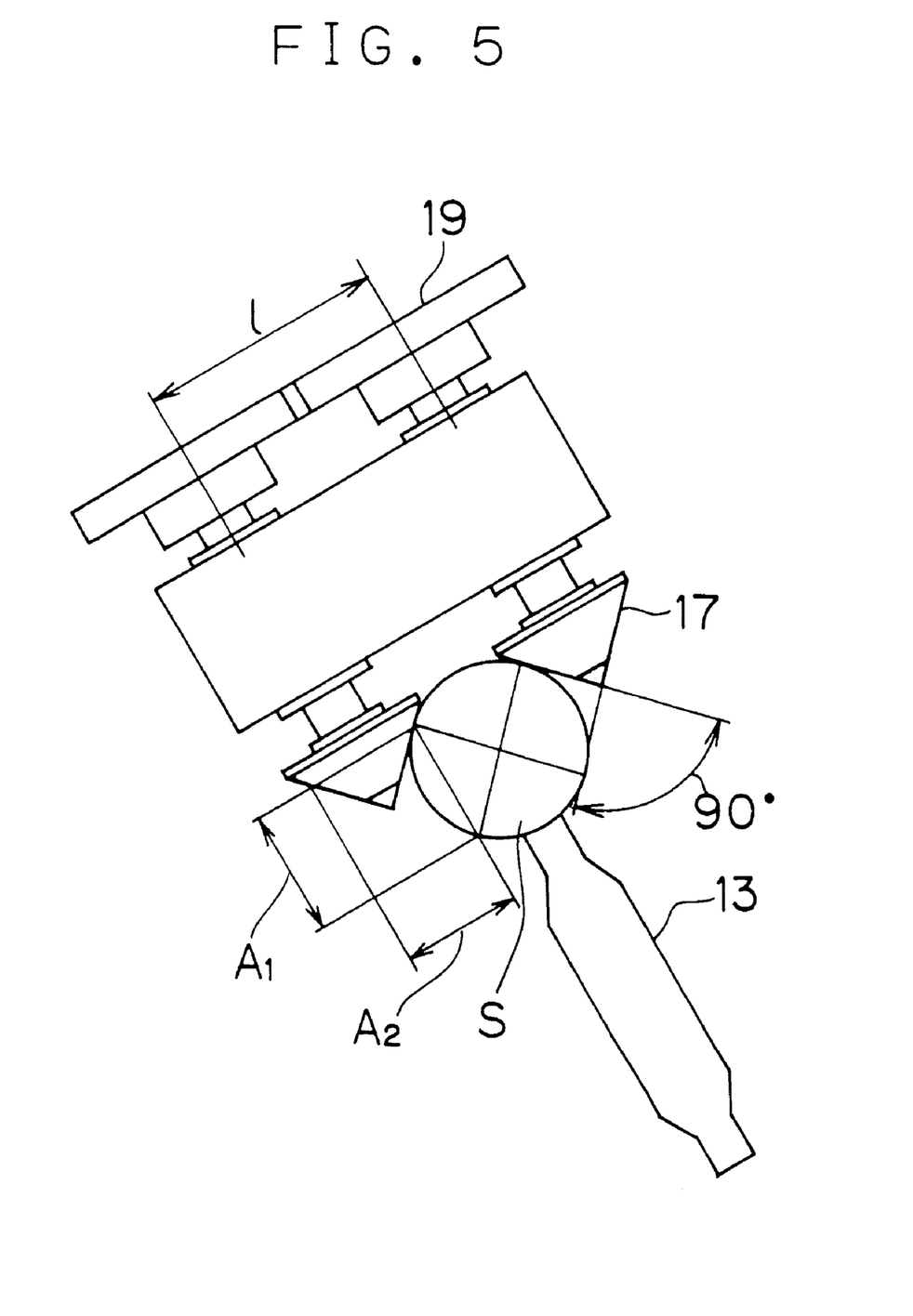
FIG. 5 is a schematic view illustrating the essential parts of the inspection mechanism.
Figure 6:
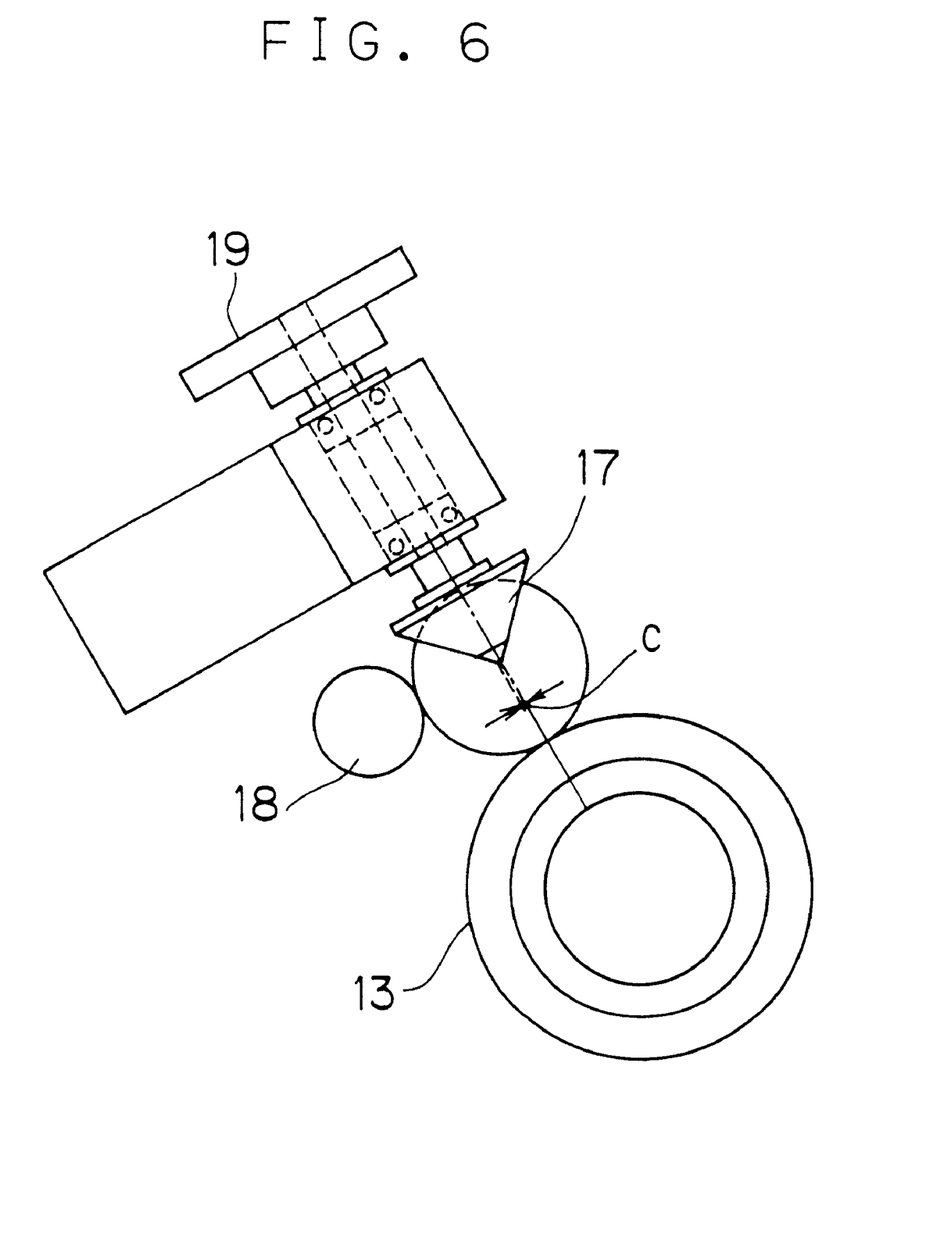
FIG. 6 is a schematic view indicating the position relations of respective elements of the inspection mechanism.

The control rollers 17 assume a set of two conical rollers (cone angle of 90°), as shown in FIGS. 5 and 6, which support the sphere thus forced together with the driving roller 13 and the support roller 18 below the sensor 16 for inspection purposes, and are attached with gears 19 at their opposite ends.

Figure 7:
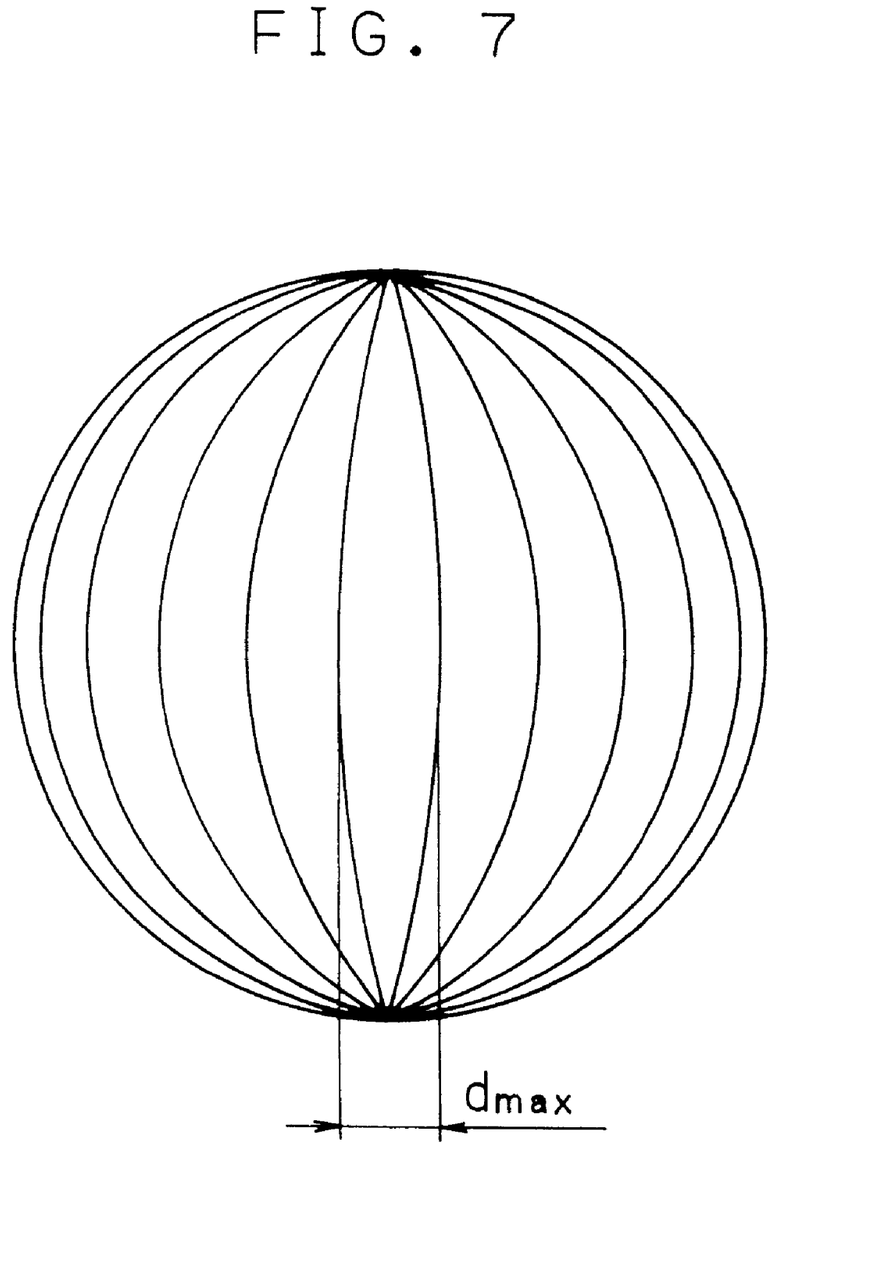
FIG. 7 is an illustration of inspection loci on a sphere detected by means of a sensor.

The rotation force of the driving roller 13 is transmitted to the sphere carried on it, and, through the sphere, further rotates the set of control rollers 17 being in contact with it. At that time, since the movement of the gears 19 at the opposite sides is transmitted to the sphere to be inspected, the gears are required to rotate lightly and silently. Consequently, their tooth profile assumes usually an excentric and helical gear, and both gears have an eccentricity of the same amount, thereby imparting a twist to the sphere. The twist causes the sphere to move in such a pattern as shown in FIG. 7 relative to the sensor 16, and eventually, the sensor 16 inspects the front surface of it.

In the vicinity of the inspection spot where each sphere supported with the driving roller 13, control rollers 17 and support roller 18 is inspected, there is disposed the discriminating gate 14. After inspection, the sphere is discriminated by means of an electric circuit in terms of non-defective or defective, and the support roller 18 is moved in the arrow direction in FIG. 4 to discharge the sphere from the inspection spot in order to screen it on the discriminating gate 14.

The sequential operation of the inspection/screening mechanism B from charging to discharging of spheres is carried out by the rotation of a cam 20 as shown in dash lines in FIG. 4 whereas the timing of the operation is regulated by means of the timing detector 15. A disc 15a for detecting signals of the timing detector 15 and a cam shaft are revolved with a motor in the same revolution number. On the other hand, the driving roller 13 is revolved with another motor M. Both motors are variable according to the size of spheres.

Figure 8:
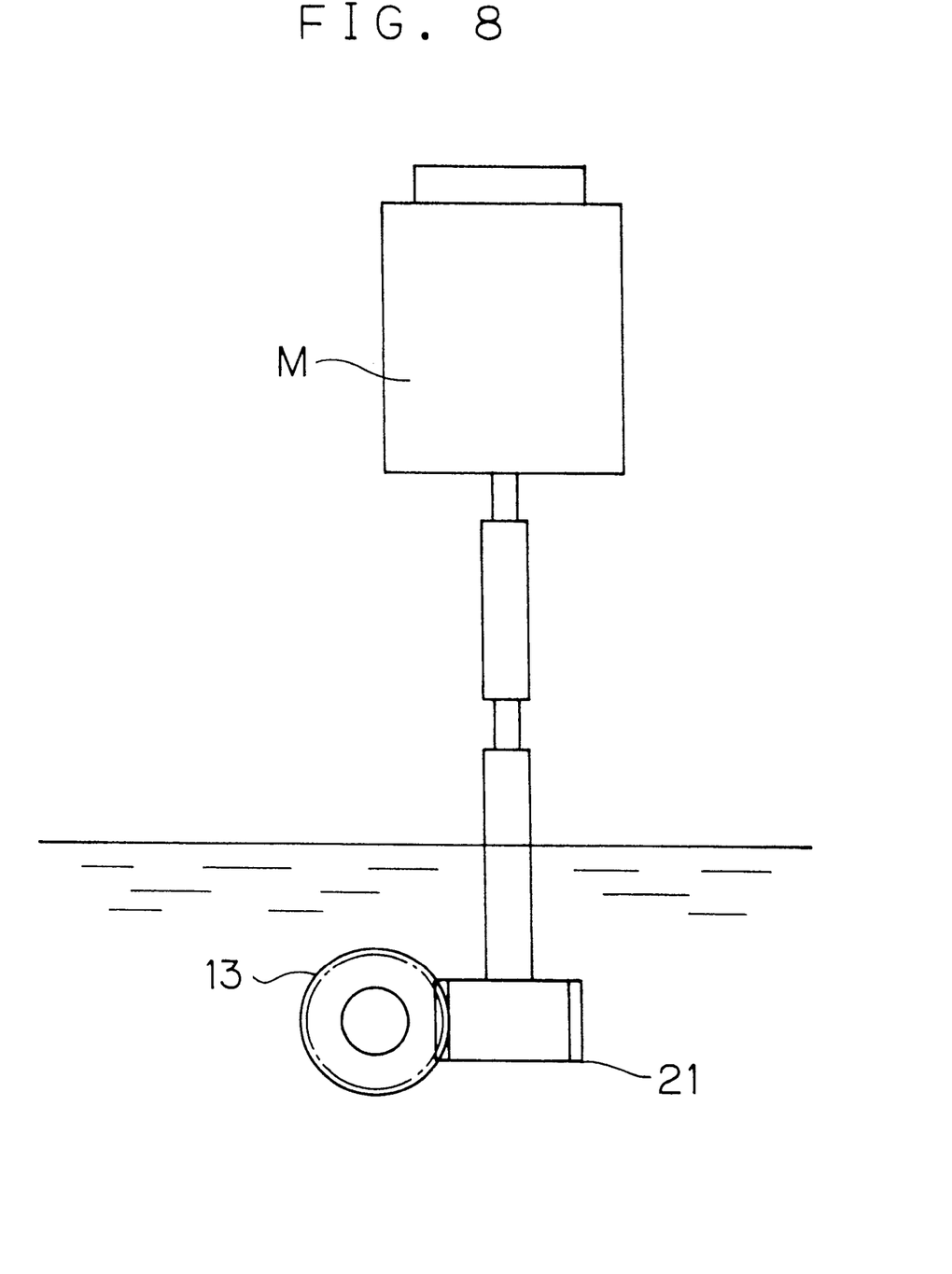
FIG. 8 is an illustration showing the drive system of a driving roller.

If bubbles are generated from any rotaty parts of the driving roller 13, etc. and migrate to the sensor 16, a "defective" signal will be transmitted. Therefore, according to this invention a contrivance for preventing the generation of bubbles is introduced. That is, the rotation of the driving roller 13 was initially relied on the transmission of a belt, which belt went into and out of oil and simultaneously entrapped air, which fact was responsible for generation of bubbles. As a consequence, in this invention, a shaft of the driving roller 13 existing in oil and a shaft connected directly to the motor M are linked through a gear wheel 21, as shown in FIG. 8, so that the rotary parts never go in and out between air and oil.

Further, where the gears 19 linking the rotation of two control rollers 17 are revolved at the oil face level bubbles will be naturally generated, but even if revolved within oil, fine bubbles will be generated because of high speed revolution. Hence the gears 19 are located to be exposed to air.

As an oil of the oil tank 7, in which respective rollers of the inspection station 8 are received, is preferred such an oil that is difficult to generate bubbles or easy to defoam even if bubbles are generated. In general a paraffinic petroleum solvent is used.

When a sphere is rotated within oil, the fictions at tangential points between the sphere and the control rollers 17 are reduced and the sphere slips. Because of this, an influence of the slip is also examined, and the position of the sphere is displaced from a normal position ($A_1=A_2$ in FIG. 5) to be rearward by the amount of c (cf FIG. 6) so that the sphere may not jump out during inspection. Thus the dimension of a distance (l) between the control rollers is set to be smaller, with the relation of $A_1>A_2$ holding true (cf. FIG. 5).

As the top portion of the sensor 16, immersed in oil, a quartz optical fiber (glass fiber) of 50 $\mu$m in diameter is chosen for use, considering oil resistance.

The shape of the sensor 16 has significant relations to its inspection width and inspection area, and furthermore greatly affects the treatment speed and screening precision. More specifically stated, the following phenomena are observed:

(1) The narrower the inspection width of the sensor, the smaller must the twist amount, i.e., a maximum distance ($d_{max}$) between lines (cf. FIG. 7) of the sphere be made. Otherwise the front surface of the sphere cannot be inspected. To that end, it is necessary to increase the frequency of revolution of the sphere during inspection, and unless the sphere is revolved at high speed, the treatment speed will be delayed.

On the other hand, the larger the sphere, the more extensive the surface area of it. Accordingly, for the same inspection width the treatment speed will be delayed more and more.

(2) For flaws of the same size, the larger the inspection area, the smaller is the signal output from the electric circuit. As a result, the more the relative magnitude to noises is reduced, which makes the detection difficult and accordingly deteriorates the screening accuracy.

(3) If an overall (100%) flaw passes within the inspection width, the detection sensitivity will be the same everwhere in the inspection width. If not 100%, the detection sensitivity naturally drops.

Figure 9A:
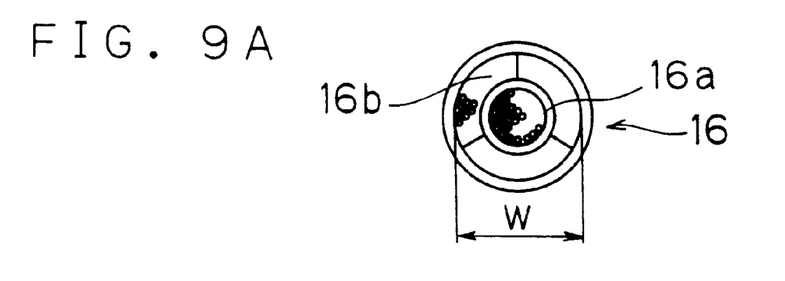
FIG. 9A, FIG. 9B and FIG. 9C show examples of branching sensors, four-branch, six-branch and six-branch, respectively.
Figure 9B:
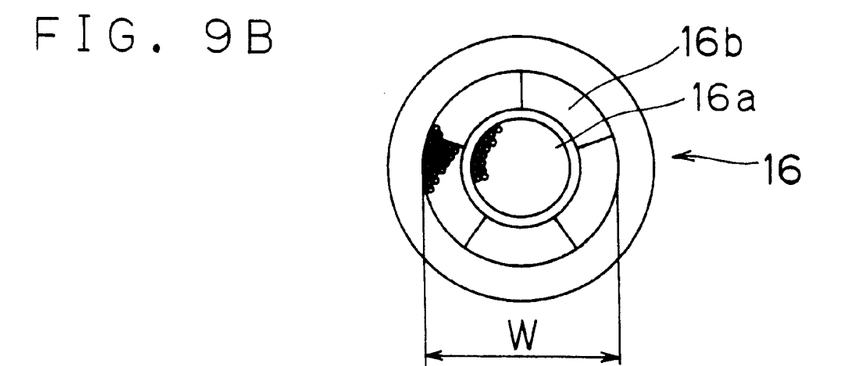
Figure 9C:
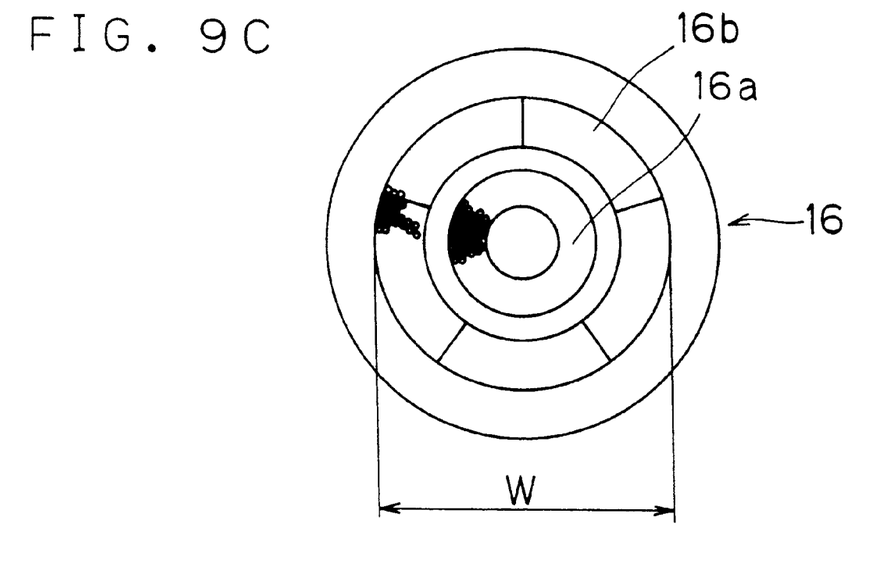

From the viewpoints above, the sensor 16 is configured as illustrated in FIG. 9A to FIG. 9C. Considering the shape of the sphere to be inspected, a light projecting part 16a is disposed in the center and a light receiving part 16b is arranged in the surrounding of the light projecting part so as to receive a reflection light from the surface of the sphere.

The rate of reflection light incident on the light receiving part 16b is decreased with a distance from the center of the sphere because the reflection light scatters more at the outward side. This tendency is larger and larger as the curvature of the sphere is increased. The reduction in quantity of the reflection light makes the signal voltage generated according to the light quantity smaller, and consequently, the signal voltage must be amplified by means of an electric circuit. This deteriorates the signal-to-noise ratio (SN ratio) and the sensitivity to flaws is deteriorated, accordingly. In order to avoid the reduction in sensitivity the receiving quantity of the reflection light must be increased, and to that end, there are two approaches conceivable, the one intensifying the light source and the other making the size of the light receiving part larger thereby to enlarge its area.

Since the intensity of the light source has its own bounds, recourse to the latter approach of enlarging the area of the light receiving part must have. The greater the area of the light receiving part, the worse is the sensitivity to flaws. However, if the dimension of the sensor 16 shown in FIG. 9C, particularly the diameter of the light receiving part 16b is made larger in order to enlarge the area, then the inspection width (W) is widened and hence, the treatment speed rises.

As described above, the sensitivity and the treatment speed of the screening mechanism are in a trade-off relation. With a view to breaking this relation and raising the treatment speed without diminishing the sensitivity, it is effective to use a branch sensor as illustrated in FIGS. 9A to 9C, wherein the light receiving part 16b is divided. That is, the light receiving part 16b on a ring is divided into sections of the same size to make their areas small so that respective sections can sense their reflection light quantities with separate electric means.

In that case, such a flaw that passes through any dividing boundary line will be captured by being divided into both light receiving sections, and accordingly caught as a smaller flaw, thus lowering the sensitivity. Therefore, the light receiving part is divided into an odd number of sections so that any flaws can pass any of the divided receiving sections whatever place in the inspection width the flaws pass.

Usually the light receiving part is divided into three or five sections according to the size of the sensor. In this way a sensor having a high sensitivity and a wide inspection width can be fabricated, with which it is possible to inspect in the same sensitivity from edge to edge of the light receiving sections.

The dimension of maximum distance ($d_{max}$) between lines (FIG. 7) must be determined according to the inspection width (W) of the sensor fabricated in accordance with the foregoing concept. To that end, inspection is conducted by setting the maximum distance smaller than the inspection width, with its edges double inspected. Besides, the eccentricity magnitude of the eccentric helical gears is determined so that the sphere may be twisted by the maximum distance. The larger the sphere, the more extensive is the inspection area. In order to shorten the inspection time as far as possible, it is preferred to make the diameter of the sensor larger thereby to make the inspection width larger. As a consequence, the maximum distance between lines and the eccentricity magnitude of the eccentric helical gears are also increased.

Figure 10:
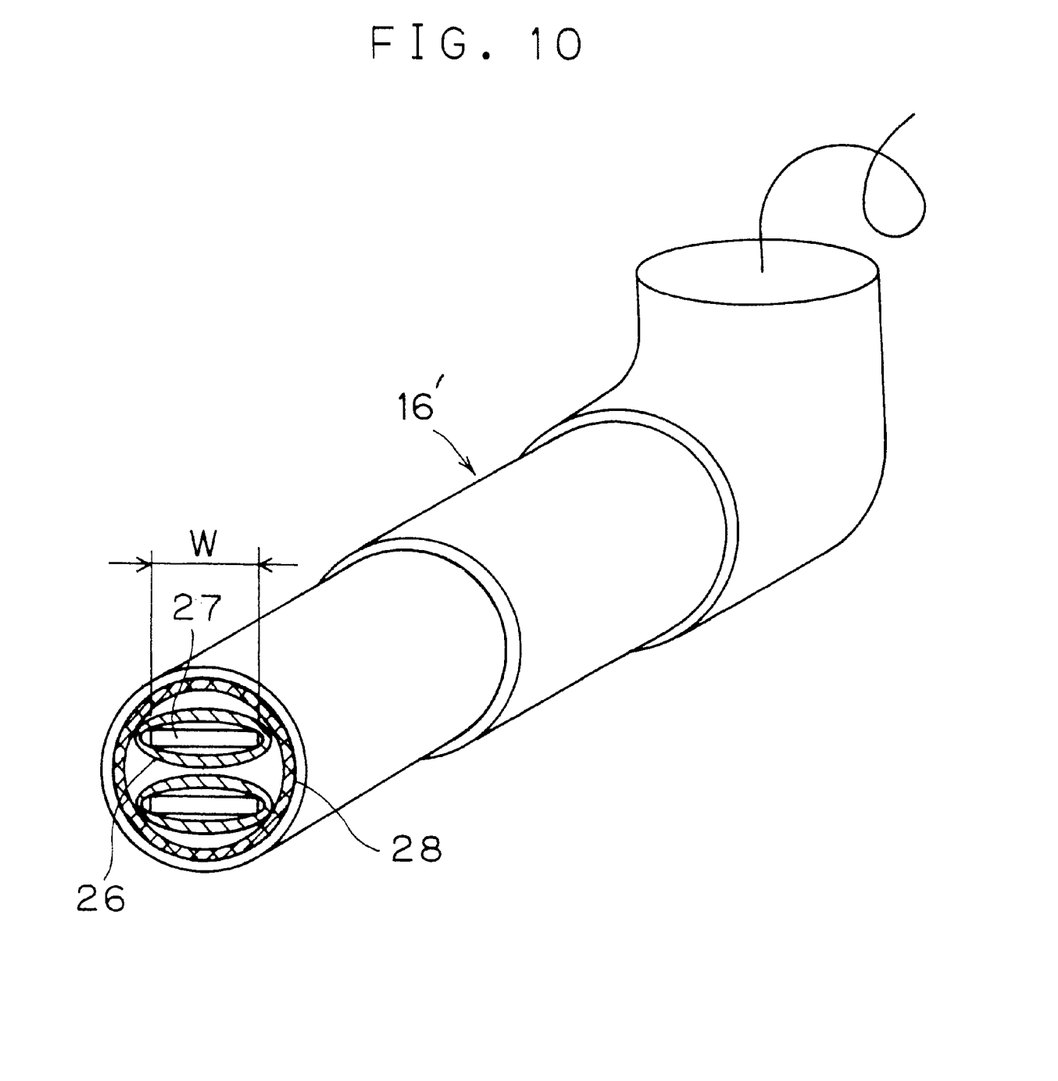
FIG. 10 is a diagrammatic perspective view of another example of a sensor showing the construction of its top end part in cross-section.

Alternatively, it is possible to use a sensor 16' of mutual induction self-comparison type as shown in FIG. 10. This is particularly suitable for inspecting steel balls which have fine cracks difficult or unable to detect. The sensor 16' assumes, at its front end part, a round rod and is comprised of two inspection coils 26 of enamel wire stacked one upon another, each of which is coiled around a ferrite core 27, and an exciting coil 28 surrounding the inner coils 26. And the sensor assumes, at its rear end part, a definite shape in top and bottom so that in use, it can be installed in the direction in which the inspection coils 26 are vertically stacked. Upon inspection, when any defect or flaw on a sphere passes through the planes of the stacked coils 26 vertically from bottom to top, therefore, signals due to the flaw are available most stably.

The inspection width W (stable inspection range) of the sensor 16' is the same as the width W of the core 27, and consequently, in order to secure a stable inspection capability, the maximum distance ($d_{max}$) is set to be the same as or narrower than the width of the core 27.

The sensor 16' is connected to a conventional eddy current test equipment not shown, with which inspection results are detected and represented. For inspection purposes, such a reference defective steel ball is used that has one flat-bottom hole (0.75 mm long×0.05 mm wide×0.05 mm deep) engraved by electric discharge machining and finished to a specular face. A sphere to be inspected is brought into rotation and signals obtained from its defect are adjusted by comparison with this reference defect, whereby the inspection sensitivity of the sensor is set.

Figure 11:
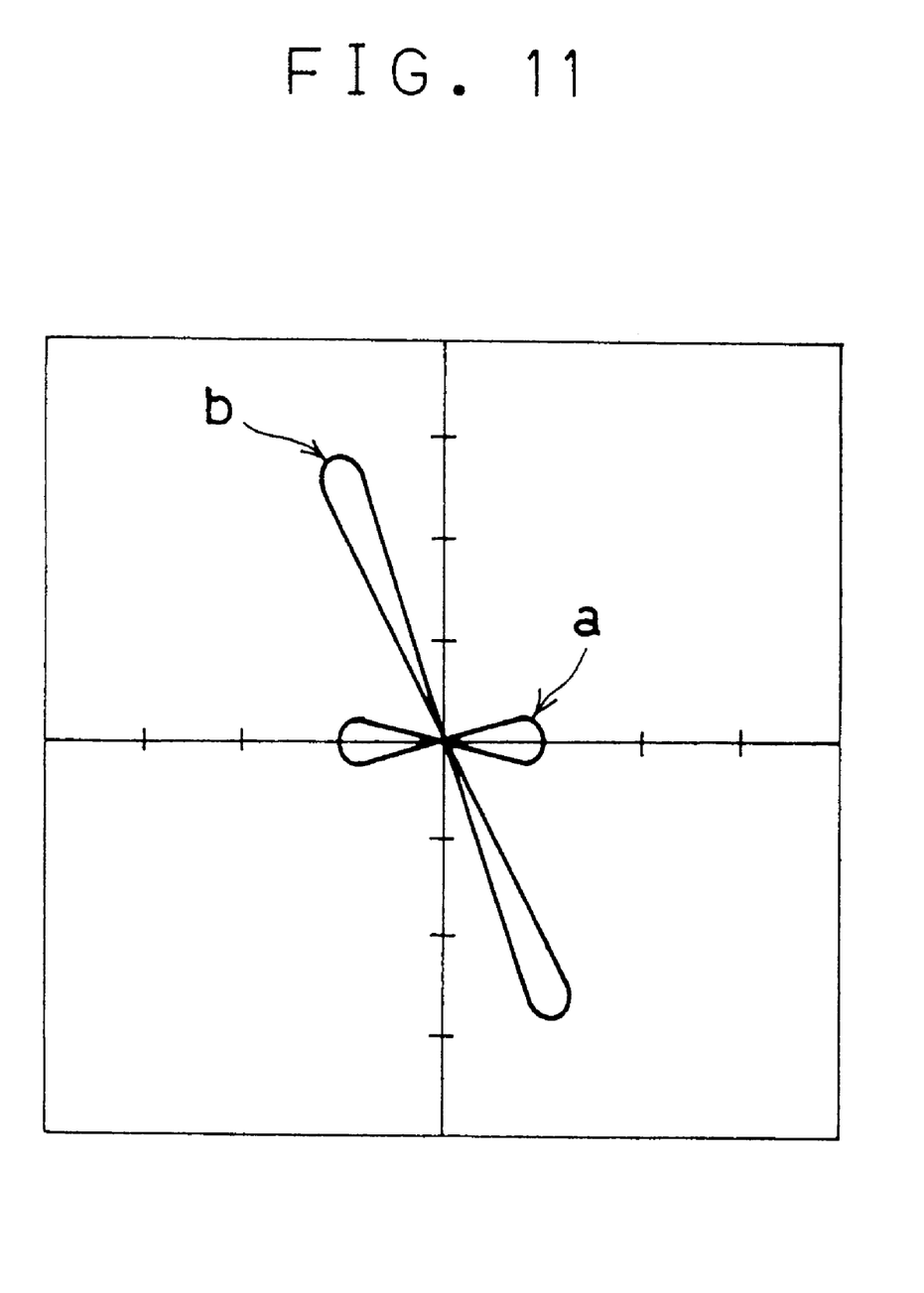
FIG. 11 is an illustration showing a display picture output from a phase detection circuit of an eddy current test equipment.

The adjustment of the signals from the sphere under inspection is conducted while watching the display screen of an oscilloscope, on which output signals are displayed as shown in FIG. 11, connected to a monitor terminal of the eddy current test equipment. Since a noise a due to the vibrations of the rotational means (13,17) and the sphere and a signal b due to the reference defect have respective phases, the adjustment is conducted so as to optimize the SN ratio by means of a phase detection circuit. In order that the noise a may be along the horizontal coordinate, the phase is adjusted and in order that the reference defect signal b projecting on the vertical coordinate may become a predetermined magnitude, the gain is adjusted. A threshold value is set to be a half the magnitude of the reference defect signal and this is chosen as a comparative standard for discrimination.

The test equipment, whose sensitivity is set by the reference defective sphere, assures the detection and judgment of a flaw as large as the size of the reference defect.

It is possible to vary the inspection scope of the sphere from the surface layer part (several ten micrometer deep from the surface) to a deep layer part (on the order of 100 micrometer deep from the surface) by switching over the exciting frequency of the sensor 16' to three tiers. The inspection up the deep part of the sphere permits to minimize the effect of noise caused in the surface layer part depending upon the processing conditions, thereby improving the SN ratio of signals.

The sensor 16 or 16' described above can be used alone or in combination thereof. In installing of the sensor to the rotational means, it is effective to fix the sensor 16 and/or 16' by the use of a positioning jig so that its center axis is directed toward the center of the sphere.

As described above, on the apparatus of this invention thus constructed, spheres in the container C, are loaded on the supply device, fed quantitatively into the cleaning device, and cleaned in a discrete state with the rotation of the nylon brushes; the spheres thus cleaned are transferred in a line to the screening device and subjected to inspection at the inspection station one by one at their surfaces with light ray, eddy current, or the like, whereby the spheres are screened automatically into non-defective and defective spheres; the spheres so screened are lifted up above the oil level among which the non-defective spheres are coated with rustproof oil, and recovered via the passage 9 to a container $C_2$ whereas the defective spheres are recovered through another passage 10 to a container $C_3$. In this way inspection of surfaces of the spheres is accomplished To summarize, this invention is concerned with the inspection apparatus wherein the primary elements of the inspection and screening mechanism are received in the oil tank, in order to conduct, after cleaning, surface inspection in oil thereby to perform automatic discrimination and screening between non-defective and defective samples. Consequently, not only is there neither the problem of causing greasy staining nor the necessity of degreasing, but also it is free from any fear of rusting even if made of a metal susceptible to rusting. Moreover, the cleaning device is compact and simplified, so that the installing space is minimized, curtailing the cost. Thus, sequentiality of the cleaning and inspection/screening steps is facilitated, and workability is also enhanced. In addition, a synergistic effect due to both the rotation of the set of conical control rollers by means of the eccentric helical gears and the rotation of the driving roller imparts a twist to each sphere, with the result that it is possible to inspect the whole surface thereof with the sensor, and consequently, further effect of heightening the inspection efficiency and inspection accuracy is obtained.

What is claimed is:

1. An inspection apparatus for inspecting surfaces of spheres which comprises a combination of: a supply device for supplying the spheres to be inspected; a cleaning device for the spheres so supplied; an inspection and screening mechanism for inspecting the spheres thus cleaned and delivered through a tubing; and a removal device for removing the spheres thus inspected separately according to the screening class and housing them in separate containers, wherein the inspection and screening mechanism includes a driving roller; alignment fingers, provided upstream of the driving roller, for putting the spheres one by one in a line onto the driving roller under rotation; a feeding roller for thrusting each sphere carried on the driving roller toward the rotational direction of the driving roller along an outer periphery thereof; a set of conical control rollers disposed to tangentially contact with the surface of the sphere thus thrusted with the outer periphery of the driving roller; a support roller, disposed adjacent to and downstream of the control rollers, for supporting the sphere; a sensor for inspecting the surface of the sphere supported on the driving roller, the set of control rollers and the support roller, while imparting a twist toward the sensor to the sphere by rotations of the driving roller and control rollers; a discriminating gate disposed at the output side of the support roller; and an oil tank holding therein the driving roller, the feeding roller, the set of control rollers, the support roller, the sensor and the discriminating gate so that the spheres can be inspected at their surfaces in the oil thereby to discriminate and screen them between non-defective and defective spheres.

2. The inspection apparatus as set forth in claim 1, wherein the cleaning device includes a rotary disc and a fixed disc which are superposed one upon another at the surface side and reverse side, respectively, of the device and held in a slanting manner, the rotary disc being defined concentrically with holes for placing therein every one of the spheres in the same pitch radially and circumferentially, the fixed disc being defined partly with a cutout for delivery of the spheres therefrom; cleaning brushes provided in contact with the rotary disc at a predetermined position in the rotational direction thereof so that the spheres supplied in the holes can be cleaned with the cleaning brushes with the rotation of the rotary disc, and the cleaned spheres can be delivered in sequence from the cutout downwardly.

3. The inspection apparatus as set forth in claim 1, wherein the sensor is an optical branch type of sensor comprised of a light projecting part at its center and a light receiving part in the surrounding of the light projecting part, the light receiving part being further divided into an odd number of sections.

4. The inspection apparatus as set forth in claim 1, wherein the sensor is of a mutual induction self-comparison type including two vertical stacked inspection coils each wound around a core of an exciting coil surrounding the coils.

5. The inspection apparatus as set forth in claim 1, wherein the oil of the oil tank is a paraffinic petroleum solvent.

6. A method for inspecting surfaces of spheres on the inspection apparatus as set forth in claim 1 which comprises sequential steps of:

supplying the spheres to be inspected to the cleaning device; cleaning them with the cleaning brushes while rotating; delivering the cleaned spheres in a line one by one to the inspection and screening mechanism; inspecting the surface of each sphere in oil, while imparting twist toward the sensor to the sphere, by means of the sensor, with each sphere supported with the driving roller, set of control rollers, and support roller and imparted with the twist by both rotations of the driving roller and control rollers; discriminating and screening the spheres between non-defective and defective spheres; and discharging both groups of the spheres separately.

7. The inspection apparatus as set forth in claim 1, wherein the sensor is a combination of an optical branch sensor comprising a light projecting part at its center and a light receiving part surrounding the light projecting part, the light receiving part being further divided into an odd number of sections, and a mutual induction self-comparison sensor comprising two vertical stacked inspection coils, each coil being wound around a core, and an exciting coil surrounding the coils.

* * * * *